US012773566B2

(12) United States Patent
Swenson et al.

(10) Patent No.: US 12,773,566 B2
(45) Date of Patent: Oct. 27, 2026

(54) PATIENT DEVICE FOR A LEADLESS PACEMAKER COMMUNICATION SYSTEM

(71) Applicant: BIOTRONIK SE & Co. KG, Berlin (DE)

(72) Inventors: Kurt Swenson, Corvallis, OR (US); Alan Fryer, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 282 days.

(21) Appl. No.: 18/685,293

(22) PCT Filed: Aug. 22, 2022

(86) PCT No.: PCT/EP2022/073321
§ 371 (c)(1),
(2) Date: Feb. 21, 2024

(87) PCT Pub. No.: WO2023/036592
PCT Pub. Date: Mar. 16, 2023

(65) Prior Publication Data

US 2024/0424310 A1 Dec. 26, 2024

Related U.S. Application Data

(60) Provisional application No. 63/242,133, filed on Sep. 9, 2021.

(30) Foreign Application Priority Data

Sep. 27, 2021 (EP) .................................... 21199026

(51) Int. Cl.
*A61N 1/372* (2006.01)
*A61N 1/375* (2006.01)

(52) U.S. Cl.
CPC ..... *A61N 1/37217* (2013.01); *A61N 1/37247* (2013.01); *A61N 1/37254* (2017.08); *A61N 1/37512* (2017.08); *A61N 1/3756* (2013.01)

(58) Field of Classification Search
None
See application file for complete search history.

(56) References Cited

U.S. PATENT DOCUMENTS

2002/0161763 A1* 10/2002 Ye .......................... G06F 21/55
2015/0073498 A1* 3/2015 Kothandaraman .......................... A61N 1/37235 607/59

(Continued)

FOREIGN PATENT DOCUMENTS

EP 1928545 A1 6/2008

OTHER PUBLICATIONS

Extended European Search Report mailed on Apr. 8, 2022, by the European Patent Office for Application No. EP21199026.2. (6 pages).

(Continued)

*Primary Examiner* — Mallika D Fairchild
(74) *Attorney, Agent, or Firm* — Buchanan Ingersoll & Rooney PC

(57) ABSTRACT

A patient device for a leadless pacemaker communication system is disclosed. The patient device is configured to receive and transmit data from and to a service device as well as from and to a leadless pacemaker. The patient device comprises a first controlling device for controlling communication from and to a service device and a second controlling device for controlling communication from and to a leadless pacemaker. The second controlling device is immutable.

17 Claims, 2 Drawing Sheets

(56) References Cited

U.S. PATENT DOCUMENTS

2020/0030618 A1* 1/2020 Holbrook ........... A61N 1/37247
2020/0086128 A1* 3/2020 Rondoni ............... G06F 21/606

OTHER PUBLICATIONS

International Search Report (PCT/ISA/210) and Written Opinion (PCT/ISA/237) mailed on Dec. 8, 2022, by the European Patent Office as the International Searching Authority for International Application No. PCT/EP2022/073321. (12 pages).

* cited by examiner

PATIENT DEVICE FOR A LEADLESS PACEMAKER COMMUNICATION SYSTEM

CROSS-REFERENCE TO RELATED APPLICATIONS

This application is the United States National Phase under 35 U.S.C. § 371 of PCT International Patent Application No. PCT/EP2022/073321, filed on Aug. 22, 2022, which claims the benefit of European Patent Application No. 21199026.2, filed on Sep. 27, 2021, and U.S. Patent Provisional Application No. 63/242,133, filed on Sep. 9, 2021, the disclosures of which are hereby incorporated by reference herein in their entireties.

TECHNICAL FIELD

The instant invention generally relates to a communication system for a leadless cardiac pacemaker device.

BACKGROUND

In recent years, leadless pacemakers have received increasing attention. Leadless pacemakers, in contrast to pacemakers implanted subcutaneously using leads extending transvenously into the heart, avoid leads in that the pacemaker device itself is implanted into the heart. Leadless pacemakers typically have the shape of a capsule for implantation into cardiac tissue, in particular the right ventricular wall of the right ventricle. Such leadless pacemakers exhibit the inherent advantage of not using leads, which can reduce risks for the patient involved with leads transvenously accessing the heart, such as the risk of pneumothorax, lead dislodgement, cardiac perforation, venous thrombosis and the like.

Leadless pacemakers may specifically be designed for implantation in the right ventricle and, in this case, during implantation are placed in or on the right ventricular wall. A ventricular pacing may, for example, be indicated in case a dysfunction at the AV node occurs, but the sinus node function is intact and appropriate. In such a case, in particular a so-called VDD pacing may be desired, involving a ventricular pacing with atrial tracking and hence requiring a sensing of atrial activity in order to pace at the ventricle based on intrinsic atrial contractions.

Remote Interrogation using the implantable leadless pacemaker inductive communications link (normally used to interface with clinician programmer) can be generally used by a patient device to obtain the same information that the programmer obtains during a normal in-clinic follow-up. In addition, remote interrogation can be used and carried out by a service center (e.g., Home Monitoring Service Center) in order to be able to ensure comprehensive care for the patient.

Secure end-to-end communications techniques are used in many systems to prevent attacks by malicious parties and to provide privacy. Leadless pacemakers try to use as much of the energy stored in their battery to support pacemaker functionality over as long a service time as possible. In addition, leadless pacemakers are implanted deep in the body where higher data throughput can only be achieved at the cost of significant energy expenditures. Consequently, no leadless pacemakers exist yet that provide encryption or other secure communications techniques in the interface used to communicate with a programmer. The main mitigation used to offset this weakness is that inductive communications requires that the implant and the programmer be located very close to each other and that such follow-ups are typically conducted in a clinical environment under the guidance of trusted physician.

Summarizing, leadless Pacemakers are not conducive to using radio frequency (RF) telemetry to do remote monitoring due to extreme low power design, but an inductive communication interface can be exploited to achieve a patient triggered remote interrogation when the circumstances warrant it. Because of the need for very high energy efficiency, the leadless pacemaker implant cannot spare the electrical energy required for typical wireless cybersecurity measures.

The present disclosure is directed toward overcoming one or more of the above-mentioned problems, though not necessarily limited to embodiments that do.

SUMMARY

It is an object of the present invention to provide elements of a leadless pacemaker communication system that allow a remote interrogation of data of a leadless pacemaker and an enhanced protection against remote attacks, such as cyber-attacks, on a leadless pacemaker.

At least this object is achieved with a patient device for a leadless pacemaker communication system having the features explained in the following. Such a patient device is designed and configured to receive and transmit data from and to a service device. The service device may be, for example, a cellular phone or a smartphone. Furthermore, the patient device is designed and configured to receive and transmit data from and to a leadless pacemaker. Thus, the patient device serves as intermediate device between a service device and a leadless pacemaker. The patient device comprises a first controlling device for controlling communication from and to a service device. The patient device further comprises a second controlling device for controlling communication from and to a leadless pacemaker. Thus, the communication capabilities of the patient device are divided into two parts, wherein the first part (comprising the first controlling device) is responsible for controlling communication from and to a service device. Likewise, the second part (comprising the second controlling device) is responsible for controlling communication from and to a leadless pacemaker. In this context, the second controlling device is immutable. Thus, it will not be possible to update or otherwise influence the general capabilities of the second controlling device.

Since the second controlling device serves for controlling communication from and to a leadless pacemaker, the immutability of the second controlling device guarantees a safe data communication between the patient device and the leadless pacemaker even if a cyber-attack or any other remote attack is directed onto the patient device. The second controlling device can be designed in an immutable manner since it only needs to handle a few very simple tasks that do not require patching or upgrading. By limiting the functionality of the second controlling device, a secure and attack-resistant communication between the patient device and the leadless pacemaker is enabled.

In an embodiment, the first controlling device is updatable. This allows keeping the patient device in sync with wireless standards applied or required by the service device. Thus, a user of the patient device can rely on the most current software available due to the updateability of the first controlling device, wherein such updateability does not negatively influence the secure communication between the patient device and the leadless pacemaker. The updateability of the first controlling device also allows required updates that might be needed to address any cybersecurity vulnerabilities that were discovered in post-market monitoring of the patient device and the communication standards applied by the patient device.

In an embodiment, the first controlling device is designed and configured to be able to be updated remotely, e.g., by mobile device management (MDM) solutions. Such solutions enable a centrally managed update of remotely arranged devices in a particularly simple and reliable manner. Such centrally managed remote update can also be denoted as fleet management of the respective devices, i.e., as fleet management of the patient device. Such centrally managed remote technologies allow the secure distribution of software to devices. They generally create the potential risk of an attack by malicious actors so that any such technologies are generally subject to vulnerability. However, even if an update process of the first controlling device would be subject to such a malicious attack, this would not influence the secure communication between the patient device and a connected leadless pacemaker due to the communication splitting in the patient device realized by the first controlling device and the second controlling device.

In an embodiment, the patient device comprises a first communication transceiver controlled by the first controlling device. This first communication transceiver serves for receiving and transmitting data from and to a service device and/or a service center in a wireless manner. All standard data transmission protocols or specifications are appropriate for such a wireless data communication. Examples of standard data transmission protocols or specifications are the Global System for Mobile Communications (GSM) standard (including its subsequent generations), the Code-division multiple access (CDMA) protocol, the Medical Device Radiocommunications Service (MICS), the Bluetooth Low Energy (BLE) protocol and the Zigbee specification.

In an embodiment, the patient device comprises a second communication transceiver controlled by the second controlling device. The second communication transceiver serves for receiving and transmitting data from and to an implantable leadless pacemaker in an inductive manner. Such inductive telemetry between a leadless pacemaker and a patient device is generally known and well established. It turned out to be a particularly reliable communication possibility over short distances. Thus, the patient device needs to be typically placed close to the (implanted) leadless pacemaker in order to establish an inductive telemetry link.

In an embodiment, the patient device comprises an interface between the first controlling device and the second controlling device. This interface only allows a limited data exchange between the first controlling device and the second controlling device. The limitation of the data exchange is defined by an intentionally limited data comprehensibility of the second controlling device. Thus, the second controlling device is intentionally made less intelligent than the first controlling device. In doing so, the first controlling device enables high-level data communication, wherein the second controlling device only enables low-level data communication. Thus, the higher-level functionality of the first controlling device enables a comfortable communication with a service device. However, the communication between the first controlling device and the second controlling device is necessarily limited to the lower-level functionality of the second controlling device. This guarantees a secure communication between the patient device and a connected leadless pacemaker, in particular via inductive telemetry, since the second controlling device cannot be compromised by high-level data requests.

Alternatively or additionally, any interface is limited based on comprehension of the receiver. Separating high- and low-level protocol may make things more secure, but not necessarily. Low level protocol is less subject to change and thus easier to make immutable. A simple interface is harder to attack as it presents a smaller attacker surface.

In an embodiment, the second controlling device is configured such that it does not allow sending a request to a leadless pacemaker device to disable a write protection mechanism of the leadless pacemaker device. Such a write protection mechanism is typically disabled by a leadless pacemaker upon initiating a communications session with a patient device or another communication device. By disabling the write protection mechanism, it is possible to reprogram the leadless pacemaker according to the medical needs of the patient to whom the leadless pacemaker is implanted. However, in an environment in which only data is to be interrogated from a leadless pacemaker, no such reprogramming is desired. By disabling the capability of the second controlling the device to send a request of disabling the write protection mechanism of the connected leadless pacemaker, the risk of any undesired attack against the patient device and a connected leadless pacemaker device is efficiently reduced or eliminated.

Alternatively or additionally to the last embodiment, the second controlling device may reject or not allow transmission of any command which is deemed inappropriate to remote interrogation. Thus, this immutable device is essentially a firewall that is aware of what commands can be passed safety and which not. The implementation may be on two processors, with or without encryption/authentication between them. The implementation may also be on the same processor where trust zones and other security features are used to isolate one execution context from another.

In an embodiment, the second controlling device is configured such that it assigns an attribute to any data request provided by the first controlling device. This attribute classifies the data request to which it is assigned as originating from a remote device. A connected leadless pacemaker will then classify incoming requests as being either remote or non-remote. If a request is classified as remote (i.e., originating from the patient device), it will not be possible to activate or deactivate certain functions of the leadless pacemaker. To give an example, the leadless pacemaker does not accept, in this embodiment, disabling its write protection mechanism if the request to disable the write protection mechanism is flagged as remote. Only an according request flagged as non-remote (or being non-flagged) would be in a position to disable the write protection mechanism. Thus, in this embodiment, there is an interaction between the second controlling device and a connected leadless pacemaker that allows secure communication between the two devices and enables activating or deactivating certain functions of the leadless pacemaker. The attribute can also be denoted as characteristic of the data request. It can be implemented, e.g., as a specific bit or sequence of bits that is automatically set by the second controlling device.

In an embodiment, the second controlling device comprises a computing circuitry and a read-only memory (ROM) comprising code to be executed on the computing circuitry. Such an implementation with a ROM makes an immutable configuration of the second controlling device particularly simple. However, generally any implementation that is able to prevent remote updates could be possible to enable an immutability of the second controlling device.

In an aspect, the present invention relates to a leadless pacemaker communication system. This leadless pacemaker communication system comprises a service device allowing a user interaction for retrieving data from a leadless pacemaker. The system further comprises a patient device, in particular a patient device according to the preceding explanations. Such patient device is configured to receive and transmit data from and to the service device as well as from and to a leadless pacemaker. The patient device comprises a first controlling device for controlling communication from and to the service device. It furthermore comprises a second controlling device for controlling communication from and to a leadless pacemaker. In this context, the second controlling device is immutable.

In an embodiment, the leadless pacemaker communication system further comprises a leadless pacemaker operatively coupled to the patient device. This operative coupling is established between the second controlling device and the leadless pacemaker. In an embodiment, the operative coupling is realized by inductive communication. Inductive communication requires a close proximity between the leadless pacemaker and the patient device.

In an embodiment, the service device is a mobile device and/or a service center device. The mobile device is located in proximity to the patient device and comprises software (e.g., realized as app) for obtaining data from the leadless pacemaker. A location in proximity is realized if a distance between the patient device and the mobile device lies in a range of from 1 cm to 1 m, in particular of from 5 cm to 90 cm, in particular of from 10 cm to 80 cm, in particular of from 20 cm to 70 cm, in particular of from 30 cm to 60 cm, in particular of from 40 cm to 50 cm. The service center device is remotely located from the patient device and comprises software for obtaining data from a leadless pacemaker. A remote location is realized if the service device is located more than 1 m away from the patient device, typically in another room or in another building, in embodiments also in another town or in another country or even in another continent.

Additionally or alternatively, there may be several concepts for how remote interrogation could be done: (1) Implant to inductive patient device to mobile phone to service center, or (2) implant to inductive patient device to service center.

In an embodiment, the mobile device is a smart watch, a cell phone, a smart phone or a tablet. It can typically establish a communication link with the patient device via a short distance wireless connection, such as Bluetooth or Bluetooth low energy (BLE). Other communication standards (in particular those referred to above) are also possible.

In an embodiment, the service center device establishes a communication link to the patient device via a long-distance communication standard such as GSM or CDMA wireless uplink.

In an embodiment, the service center device establishes a connection to the patient device with the help of a mobile device as intermediate service device. This mobile device can be the mobile device from one of the embodiments described above. Then, the service center device communicates in a wireless manner with the mobile device, wherein the mobile device communicates in a wireless manner with the patient device. In doing so, the patient device does not need to be equipped with a communication module enabling a long-distance wireless communication. Rather, this functionality will be provided by the mobile device being located in proximity to the patient device so that a first wireless link is established between the patient device and the mobile device, and a second wireless link is established between the mobile device and the service center device.

In an embodiment, the service center device has access to a database such as a remotely managed database. Typically, a user accessible graphical user interface is offered to allow a user interaction with the service center device and the connected further devices such as a leadless pacemaker implanted into a patient.

In an aspect, the present invention relates to a method for enabling secure communication between a patient device and a leadless pacemaker. This method comprises the steps explained in the following.

First, a request for retrieval of data of the leadless pacemaker is received from a service device. This receiving is performed under control of a first controlling device.

Afterwards, the received request is sent to a leadless pacemaker. This sending is done under the control of a second controlling device.

Afterwards, a response from the leadless pacemaker is received under the control of the second controlling device. Finally, the response is sent to the service device under the control of the first controlling device. In this context, the second controlling device is immutable. As outlined above, this split of the communication realized by the service device into a first part (between the first controlling device and the service device) and a second part (between the second controlling device and the leadless pacemaker) together with an immutable configuration of the second controlling device ensures a safe communication between the patient device and the leadless pacemaker that is resistant against remote attacks such as cyberattacks. Thus, the method allows an interrogation of leadless pacemaker data using, e.g., inductive communication, without providing an attack surface by which the patient device could be remotely manipulated such to alter the state of the leadless pacemaker.

Alternatively or additionally, between all used devices and/or components of the devices encryption and/or authentication may be used to ensure communication between them is private and authentic.

All embodiments of the patient device can be combined in any desired way and can be transferred either individually or in any arbitrary combination to the leadless pacemaker communication system and to the described communication method. Likewise, all embodiments of the leadless pacemaker communication system can be combined in any desired way and can be transferred either individually or in any arbitrary combination to the patient device and to the described communication method. Furthermore, all embodiments of the described communication method can be combined in any desired way and can be transferred either individually or in any arbitrary combination to the patient device and to the leadless pacemaker communication system.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Further details of aspects of the present invention will be explained in the following making reference to exemplary embodiments and accompanying Figures. In the Figures.

DETAILED DESCRIPTION

Figure 1:
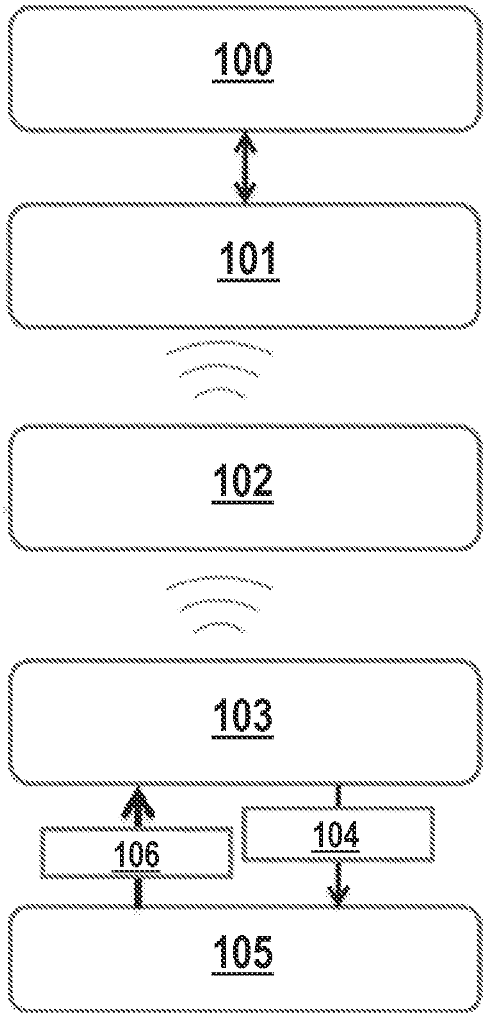
FIG. 1 (Prior Art)
FIG. 1 shows a communication path known from prior art for remote interrogations of a leadless pacemaker.

FIG. 1 shows a communications path known from prior art serving for remote interrogations of a leadless pacemaker. For this communications path, a user can operate a user accessible graphical user interface (GUI) 100. This GUI 100 is connected to a remotely managed database 101 in a service center. This remotely managed database 101 is able to communicate via GSM with a cellular phone 102 comprising an app serving to communicate with a patient device 103 also in a wireless manner. For this wireless connection between the cellular phone 102 and the patient device 103, typically a Bluetooth connection is used. The patient device 103 sends interrogation commands 104 to a leadless pacemaker 105. The leadless pacemaker 105 sends the requested data 106 back to the patient device 103. From there, it can be provided to the cellular phone 102 and can be displayed in the app of the cellular phone 102. Furthermore, the data can be further transmitted to the remotely managed database 101.

Figure 2:
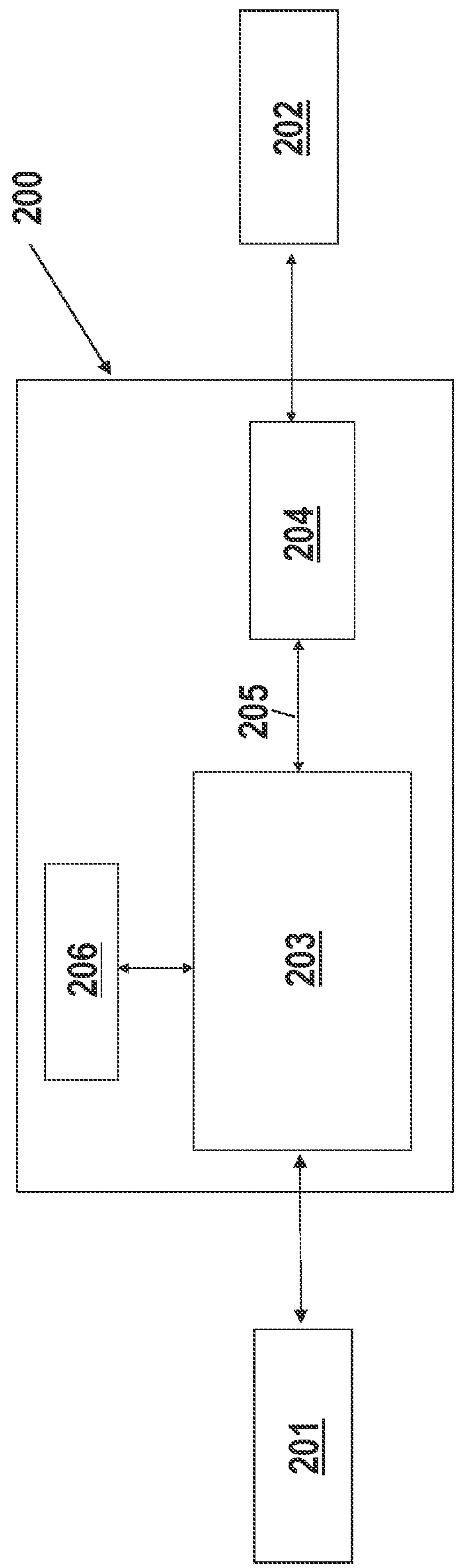
FIG. 2 shows an embodiment of a patient device enabling secure communication with a leadless pacemaker.

FIG. 2 shows a patient device 200 serving to bridge communication between a service device 201, in this example a cellular phone 201 and a leadless pacemaker 202 that is implanted into a patient in need thereof. The patient device 200 comprises a first controlling device 203 serving as first controlling device. The first controlling device 203 serves for communication between the patient device 200 and the cellular phone 201. This first controlling device 203 is updatable and allows data communication of high-level functionality. The data communication between the first controlling device 203 and the cellular phone 201 is realized via a Bluetooth connection.

The patient device 200 further comprises a second controlling device 204 serving as second controlling device. The second controlling device 204 serves for establishing a wireless communication with the leadless pacemaker 202 via inductive telemetry. An interface 205, here a hardware bus interface 205, serves for enabling communication between the first controlling device 203 and the second controlling device 204.

The second controlling device 204 only enables a lower-level communication between the patient device 200 and the leadless pacemaker 202. Due to this lower-level functionality of the second controlling device 204, the hardware bus interface 205 also limits the possibility of data exchange between the first controlling device 203 and the second controlling device 204 to such data that is understandable by the second controlling device 204. Expressed in other words, the hardware bus interface 205 only allows a data exchange between the first controlling device 203 and the second controlling device 204 on a limited level that corresponds to the lower-level functionality of the second controlling device 204. This guarantees that only comparatively simply requests can be received by the second controlling device 204 and can be forwarded from the second controlling device 204 to the leadless pacemaker 202.

The second controlling device 204 is immutable. Thus, it is not possible to update or otherwise patch the second controlling device 204. Consequently, the functionality given to the second controlling device 204 during manufacturing of the patient device 200 remains the same over the whole lifetime of the second controlling device 204. Thus, the kind of data communication between the second controlling device 204 and the leadless pacemaker 202 is defined during the manufacturing process of the patient device 200 and is immune against remote attacks seeking for compromising the functions of the leadless pacemaker 202. Furthermore, the hardware bus interface 205 is also made immutable so as not to be vulnerable to any remote security attack.

The split architecture of the patient device 200 employing the first controlling device 203 for external communication and the second controlling device 204 for communication with the leadless pacemaker 202 guarantees for a secure data communication between the patient device 200 and the leadless pacemaker 202 that cannot be compromised by external attacks.

The patient device 200 further comprises user interface elements 206 that are operatively coupled to the first controlling device 203. By these user interface elements 206 (such as buttons, LEDs, a display, a GUI or other hardware, software or graphical elements), it is possible to allow a user interaction with the patient device 200 or to indicate the status of the patient device 200 to a user such as a patient. Since the first controlling device 203 is made updatable, it can employ the latest developments in data transmission standards required for a safe and up-to-date data communication with the cellular phone 201. Thus, a user using an app on the cellular phone 201 will enjoy an easy, reliable and up-to-date communication with the patient device 200. Nonetheless, due to the provision of the second controlling device 204, secure and attack-resistance communication between the patient device 200 and the leadless pacemaker device 202 is realized.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. A patient device for a leadless pacemaker communication system, wherein the patient device is configured to receive and transmit data from and to a service device as well as from and to a leadless pacemaker, wherein the patient device comprises:

a first controlling device for controlling communication from and to a service device;

a second controlling device for controlling communication from and to a leadless pacemaker;

wherein the second controlling device is immutable;

wherein the patient device comprises an interface between the first controlling device and the second controlling device, wherein the interface only allows a data exchange between the first controlling device and the second controlling device that is limited by an intentionally limited data comprehensibility of the second controlling device.

2. The patient device according to claim 1, wherein the first controlling device is updateable.

3. The patient device according to claim 1, wherein the patient device comprises a first communication transceiver controlled by the first controlling device and serving for receiving and transmitting data from and to a service device in a wireless manner.

4. The patient device according to claim 1, wherein the patient device comprises a second communication transceiver controlled by the second controlling device and serving for receiving and transmitting data from and to a leadless pacemaker in an inductive manner.

5. The patient device according to claim 1, wherein the second controlling device is configured such that it does not allow sending a request to a leadless pacemaker to disable a write protection mechanism of the leadless pacemaker.

6. The patient device according to claim 1, wherein the second controlling device is configured such that it assigns an attribute to any data request being provided from the first controlling device, wherein the attribute classifies the data request to which it is assigned as originating from a remote device.

7. The patient device according to claim 1, wherein the second controlling device comprises a computing circuitry and a read-only memory comprising code to be executed on the computing circuitry.

8. The patient device according to claim 1, wherein the second controlling device comprises an interface configured for limiting communication of the second controlling device to inductive telemetry between the second controlling device and the leadless pacemaker.

9. A leadless pacemaker communication system, comprising:

a service device allowing a user interaction for retrieving data from a leadless pacemaker;

a patient device configured to receive and transmit data from and to the service device as well as from and to a leadless pacemaker, in particular a patient device according to any of the preceding claims, wherein the patient device comprises:

a first controlling device for controlling communication from and to the service device;

a second controlling device for controlling communication from and to a leadless pacemaker;

wherein the second controlling device is immutable;

wherein the patient device comprises an interface between the first controlling device and the second controlling device, wherein the interface only allows a data exchange between the first controlling device and the second controlling device that is limited by an intentionally limited data comprehensibility of the second controlling device.

10. The leadless pacemaker communication system according to claim 9, further comprising a leadless pacemaker operatively coupled to the patient device.

11. The leadless pacemaker communication system according to claim 9, wherein the service device is a service center device being remotely located from the patient device and comprising software for obtaining data from a leadless pacemaker.

12. The leadless pacemaker communication system according to claim 11 further comprising a mobile device, wherein the service center device is configured to establish a connection to the patient device with the help of the mobile device as an intermediate service device.

13. The leadless pacemaker communication system according to claim 9, wherein the service device is a mobile device being located in proximity to the patient device and comprising software for obtaining data from a leadless pacemaker.

14. The leadless pacemaker communication system according to claim 12, wherein the mobile device is a smart watch, a cell phone, a smart phone or a tablet.

15. The leadless pacemaker communication system according to claim 9, wherein the second controlling device comprises an interface configured for limiting communication of the second controlling device to inductive telemetry between the second controlling device and the leadless pacemaker.

16. A method for enabling safe communication between a patient device and a leadless pacemaker, the method comprising the following steps:

receiving, under control of a first controlling device, a request for retrieval of data of a leadless pacemaker from a service device;

sending, under control of a second controlling device, the request to the leadless pacemaker;

receiving, under control of the second controlling device, a response from the leadless pacemaker;

sending, under control of the first controlling device, the response to the service device;

limiting data exchange between the first controlling device and the second controlling device by an intentionally limited data comprehensibility of the second controlling device;

wherein the second controlling device is immutable.

17. The method according to claim 16, further comprising limiting communication of the second controlling device to inductive telemetry between the second controlling device and the leadless pacemaker.

* * * * *